(12) United States Patent
Lalgudi et al.

(10) Patent No.: US 8,623,653 B2
(45) Date of Patent: Jan. 7, 2014

(54) TERAHERTZ CORROSION DETECTION METHOD

(75) Inventors: Ramanathan S. Lalgudi, Westerville, OH (US); Barry L. McGraw, Westerville, OH (US); Robert J. Cain, Lewis Center, OH (US)

(73) Assignee: Battelle Memorial Institute, Columbus, OH (US)

( * ) Notice: Subject to any disclaimer, the term of this patent is extended or adjusted under 35 U.S.C. 154(b) by 186 days.

(21) Appl. No.: 12/934,369

(22) PCT Filed: Apr. 9, 2009

(86) PCT No.: PCT/US2009/040061
§ 371 (c)(1),
(2), (4) Date: Nov. 18, 2010

(87) PCT Pub. No.: WO2009/126802
PCT Pub. Date: Oct. 15, 2009

(65) Prior Publication Data
US 2011/0053275 A1 Mar. 3, 2011

Related U.S. Application Data

(60) Provisional application No. 61/123,572, filed on Apr. 9, 2008.

(51) Int. Cl.
*G01N 33/20* (2006.01)
*G01N 31/22* (2006.01)

(52) U.S. Cl.
USPC ...... 436/6; 436/5; 436/73; 436/164; 436/166; 436/172

(58) Field of Classification Search
USPC .............. 436/5–6, 73, 164, 166, 172
See application file for complete search history.

(56) References Cited

U.S. PATENT DOCUMENTS

| 4,044,253 A | 8/1977 | Crane |
| 4,278,508 A | 7/1981 | White et al. |

(Continued)

FOREIGN PATENT DOCUMENTS

| GB | 2425835 A | 11/2006 |
| WO | WO9808114 | 2/1998 |
| WO | WO2006120389 A1 | 11/2006 |
| WO | WO2007025107 A2 | 3/2007 |

OTHER PUBLICATIONS

Johnson et al., Using Flurorescent Compounds as Early Warning Detectors for Corrosion, Materials Performance, Apr. 1994, vol. 33, No. 4, pp. 25-29.

(Continued)

*Primary Examiner* — Arlen Soderquist
(74) *Attorney, Agent, or Firm* — MacMillan, Sobanski & Todd, LLC

(57) ABSTRACT

A corrosion detection product is a coating including a film forming material and a complexing agent, the complexing agent forming a complex when it comes into contact with a corrosion byproduct produced by corrosion of a substrate on which the coating is applied, the complex being detectably different from the complexing agent when the coating is exposed to radiation in order to detect the corrosion, the complexing agent being immobilized in the coating to reduce leaching of the complexing agent or the complex from the coating.

5 Claims, 1 Drawing Sheet

(56) References Cited

U.S. PATENT DOCUMENTS

| | | | | |
|---|---|---|---|---|
| 4,647,220 | A * | 3/1987 | Adams et al. | 374/5 |
| 4,758,312 | A | 7/1988 | Hunt et al. | |
| 4,795,794 | A * | 1/1989 | Winnik et al. | 526/259 |
| 4,925,268 | A * | 5/1990 | Iyer et al. | 385/12 |
| 5,208,489 | A * | 5/1993 | Houston | 326/98 |
| 5,256,187 | A * | 10/1993 | Gefvert | 75/717 |
| 5,326,389 | A | 7/1994 | Cambon | |
| 5,362,812 | A * | 11/1994 | Holmes et al. | 525/274 |
| 5,646,400 | A | 7/1997 | Perez et al. | |
| 5,774,603 | A * | 6/1998 | Moore et al. | 385/12 |
| 6,001,936 | A * | 12/1999 | Barrera et al. | 525/454 |
| 6,495,352 | B1 * | 12/2002 | Brinker et al. | 435/176 |
| 6,495,833 | B1 * | 12/2002 | Alfano et al. | 250/341.8 |
| 6,524,382 | B1 * | 2/2003 | Bujard et al. | 106/493 |
| 6,534,569 | B2 * | 3/2003 | Mahmud et al. | 523/333 |
| 6,589,779 | B1 * | 7/2003 | McDevitt et al. | 435/288.7 |
| 6,644,917 | B2 | 11/2003 | Zhao et al. | |
| 6,986,287 | B1 | 1/2006 | Dorfman | |
| 7,052,737 | B2 * | 5/2006 | Kool et al. | 427/256 |
| 7,145,148 | B2 | 12/2006 | Alfano et al. | |
| 7,244,500 | B2 | 7/2007 | Watts et al. | |
| 7,274,443 | B2 | 9/2007 | Ponstingl et al. | |
| 7,390,462 | B2 * | 6/2008 | Rao et al. | 422/82.08 |
| 7,390,560 | B2 | 6/2008 | Wallach | |
| 7,597,936 | B2 * | 10/2009 | Smith et al. | 427/419.1 |
| 2005/0084630 | A1 * | 4/2005 | Kasperchik et al. | 428/32.34 |
| 2006/0172431 | A1 * | 8/2006 | Baker et al. | 436/127 |
| 2006/0228256 | A1 * | 10/2006 | McDevitt et al. | 422/82.05 |
| 2006/0251687 | A1 * | 11/2006 | Lapidot et al. | 424/401 |
| 2007/0044704 | A1 * | 3/2007 | Osborne et al. | 116/206 |
| 2007/0048867 | A1 * | 3/2007 | Farmer | 436/6 |
| 2008/0249209 | A1 * | 10/2008 | Trummer et al. | 523/200 |

OTHER PUBLICATIONS

Alodan et al., Detection of Localized Corrosion Using Fluorescence Microscopy, Resume/Abstract, Journal of the Electrochemical Society, 1997, vol. 144, No. 10, abstract only.

Szunerits et al., Aluminum Surface Corrosion and the Mechanism of Inhibitors Using pH and Metal Ion Selective Imaging Fiber Bundles, Abstract, Analytical Chemistry, 2002, vol. 74, No. 4, abstract only.

Sibi et al., Determination of Corrosion on Aluminum Alloy Under Protective Coatings Using Fluorescent Probes, Progress in Organic Coatings, Resume/Abstract, 2003, vol. 4, No. 1, abstract only.

Smart Coatings, Corrosion Monitoring Information, www.corrosion-club.com/smart.htm, 2004, two pages.

* cited by examiner

TERAHERTZ CORROSION DETECTION METHOD

CROSS-REFERENCE TO RELATED APPLICATIONS

This application claims the benefit of U.S. Provisional Application No. 61/123,572, filed Apr. 9, 2008, the disclosure of which is incorporated herein by reference.

BACKGROUND OF THE INVENTION

This invention relates in general to corrosion detection methods, and in particular to a corrosion detection product and method that can be used to detect the corrosion of metals. Corrosion related deterioration of metallic structures can cause problems in many situations. For example, corrosion of the metallic structures of aging aircraft may reduce flight availability and service lifetime, may require costly repairs, and may result in potentially unsafe operating conditions if undetected. Several preventative and detection methods have been developed to address the problem of corrosion degradation. However, new techniques are still needed to detect corrosion on aircraft, bridges, oil pipelines and other metallic structures.

SUMMARY OF THE INVENTION

A corrosion detection product comprises a coating including a film forming material and a complexing agent, the complexing agent forming a complex when it comes into contact with a corrosion byproduct produced by corrosion of a substrate on which the coating is applied, the complex being detectably different from the complexing agent when the coating is exposed to radiation in order to detect the corrosion, the complexing agent being immobilized in the coating to reduce leaching of the complexing agent or the complex from the coating.

A corrosion detection method comprises: (a) providing a coating including a film forming material and a complexing agent, the complexing agent being immobilized in the coating to reducing leaching; (b) applying the coating on a substrate that produces a corrosion byproduct when it corrodes, the complexing agent and the corrosion byproduct forming a complex when they come into contact with each other; and (c) exposing the coating to radiation which causes the complex to be detectably different from the complexing agent in order to detect the corrosion.

DETAILED DESCRIPTION OF THE PREFERRED EMBODIMENT

Figure 1:
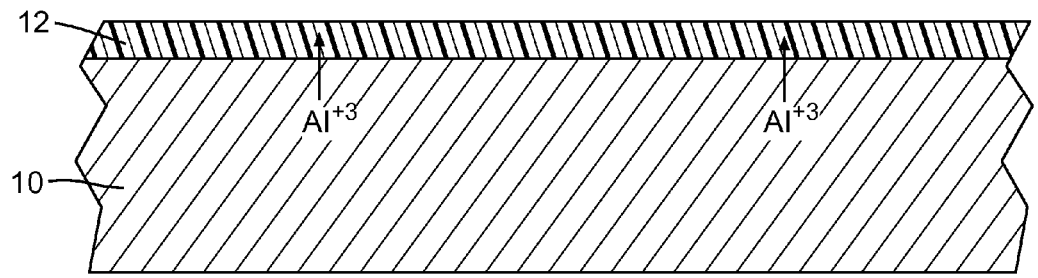
FIGS. 1 and 2 are schematic representations of a corrosion detection product and method according to the invention.

The present invention relates to a corrosion detection product and method. The product is a coating that can be applied on a substrate to detect corrosion of the substrate. Any general type of coating suitable for this purpose can be used, such as a paint, primer, lacquer, glaze or the like.

The coating includes a complexing agent that forms a complex when it comes into contact with a corrosion byproduct produced by corrosion of a substrate on which the coating is applied. The corrosion byproduct can be anything capable of forming the complex with the complexing agent. For example, the corrosion byproduct may be a metal ion that is given off from a metal surface when it corrodes. This can be any type of metal, for example, a transition metal such as aluminum or magnesium.

The complex is detectably different from the complexing agent when the coating is exposed to radiation in order to detect the corrosion. Any suitable complexing agent or a combination of different ones can be used. In some examples the complexing agents are quinolines. Some particular non-limiting examples of complexing agents that may be suitable are shown in the following Table 1:

TABLE 1

Examples of Complexing Agents

2-Amino-8-quinolinol
8-Quinolinol N-oxide
2,8-Quinolinediol
8-Hydroxy-2-quinolinecarbonitrile
8-Hydroxy-2-quinolinecarbonitrile
8-Hydroxy-2-quinolinecarboxaldehyde
5,7-Dimethyl-8-quinolinol
8-Methoxy-2-methylquinoline
8-Ethoxyquinoline
5-Nitroso-quinolin-8-ol
5-Chloro-8-quinolinol
8-Hydroxy-2-quinolinecarboxylic acid
8-Hydroxy-5-nitroquinoline
6-Nitroquinolin-8-ol
4-Acridinol
6-Amino-4,5-dimethyl-8-methoxyquinoline
Xanthurenic acid (4,8-dihydroxy-2-quinolinecarboxylic acid)
5,7-Dichloro-8-quinolinol
5-Chloro-8-hydroxyquinoline hydrochloride
5-Chloro-7-nitro-8-quinolinol
8-Hydroxyquinoline-5-sulfonic acid
8-Hydroxy-2-quinolinesulfonic acid monohydrate
9-Hydroxy-4-methoxyacridine
8-Quinolyl 3-methylcrotonate
5,7-Dichloro-8-quinaldinol
8-Quinolyl N-allylcarbamate
N-(2-(quinolin-8-yloxy)-ethyl)-acetamide
8-Quinolyl N-isopropylcarbamate
5-Amino-8-hydroxyquinoline dihydrochloride
2-Amino-8-quinolinol
8-Quinolinol N-oxide
Imidazole, Oxazole, thiazole and their derivatives
Benzimidazole, benzoxazole, benthiazole and their derivatives The coating also includes a film forming material that forms a film on a surface of the coated substrate, and that usually imparts adhesion of the coating to the substrate and binds together the other coating components. Any suitable type of film forming material or a combination of different ones can be used in the coating. Some examples are latex-based binders and alkyd-based binders which result in what are known as latex paints and alkyd paints. Some film forming materials are synthetic or natural resins. Examples of synthetic resins that may be suitable include film forming polymers such as acrylates, urethanes, epoxys, silicones, fluoropolymers, vinyl polymers, polyesters, alkyds, butadienes, styrenes, and the like. In a particular example, the film forming material is a polyurethane emulsion such as FLEXBOND® from Air Products and Chemicals, Inc.

In one aspect of the corrosion detection product, the complexing agent is immobilized in the coating to reduce leaching of the complexing agent or the complex from the coating, for example, under conditions in which the coating is exposed to high humidity or to rainfall or other water. The complexing agent can be immobilized in any suitable manner.

For example, in one embodiment the complexing agent is immobilized by being part of the film forming polymer. The complexing agent can be attached to either the main chain or a side chain of the polymer, and it can be included in any suitable amount. In a particular example, a graft copolymer includes a film forming polymer with the complexing agent attached as side chains.

In another embodiment, the complexing agent is immobilized by being tethered to a water insoluble metal oxide in the coating. Any suitable water insoluble metal oxide or a combination of different ones can be used. In some examples, the metal oxide is selected from the group consisting of titania, zirconia, silica, magnesia, alumina, and mixtures thereof.

In yet another aspect of the corrosion detection product, the complexing agent and the complex are significantly different from each other in at least one property selected from the group consisting of density, refractive index, dipole moment, polarizability, conductivity, permeability, vapor pressure, melting point, heat capacity, and water of hydration. The difference in properties may aid in the detection of the corrosion. In one aspect, the difference between the energy band gap of the complex and the energy band gap of the complexing agent is at least about 1 eV, and in some examples at least about 2 eV, where the energy band gap is defined as the difference between the highest occupied molecular orbital and the lowest unoccupied molecular orbital. This is described in more detail hereinbelow.

The coating may also include any type of solvent, or any combination of different solvents, suitable for use in coatings. When the coating is applied on an substrate, the solvent evaporates leaving behind the other coating components on the surface of the substrate. The solvent acts as the carrier for the other components and adjusts the viscosity of the coating. If a latex-based binder is used, the solvent is usually aqueous and if an alkyd-type binder is used, the solvent is usually non-aqueous. Examples of aqueous-based solvents include water, and water-based solutions such as water-alcohol mixtures and the like. Examples of non-aqueous solvents include organic-based solvents such as toluene, ketones such as methylethyl ketone or methylisobutyl ketone, benzene, ethyl acetate, white spirit, alkanes, cycloalkanes, other aromatic compounds, and isoparaffinic solvents. In a particular embodiment the solvent is water, such as the polyurethane emulsion described above.

Besides the above-mentioned components, the coating can optionally also include one or more other components suitable for use in coatings. For instance, such components may include pigments, thickeners, extenders, dispersants, lubricants, wetting agents, suspension aids, thixotropic agents, crosslinkers, water repellants, and the like.

The coating can be produced in any suitable manner, for example by combining the components in a mixer, disperser, mill or other suitable apparatus. The components can be combined in any suitable order.

The coating is applied on a substrate in any suitable manner such as by air-spraying, brushing, rolling, or other means of applying coatings. The coating can be applied in any thickness suitable for providing corrosion detection.

The substrate can be any type that produces a corrosion byproduct when it corrodes. Some examples are metallic substrates such as aluminum, steel, iron, nickel or copper. Also, the corrosion byproduct can be any type that forms a complex when it comes into contact with the complexing agent. This can be any type of complex. For example, the corrosion byproduct may be a metal ion that forms a coordination complex with the complexing agent.

The coating is exposed to radiation which causes the complex formed by the corrosion byproduct and the complexing agent to be detectably different from the complexing agent alone. This detectable difference enables the detection of corrosion of the substrate. Any suitable type of radiation or combinations of different types can be used to achieve any suitable detectable difference. For example, some radiations that may be suitable include ultraviolet, infrared, terahertz, microwave, or others. In a particular nonlimiting example, the complex formed by the reaction of a complexing agent and a metal ion corrosion byproduct fluoresces in the presence of ultraviolet radiation. This fluorescence enables early detection of corrosion of the substrate. In other examples, the complex formed may be detectable by phosphorescence, other forms of photoluminescence, or any other detectable difference.

In some embodiments, a terahertz (THz) radiation is used to detect the difference between the complexing agent and the complex formed by the corrosion byproduct. The use of THz can have some particular advantages in some embodiments as explained by the following:

Concept validation using quantum mechanical calculations

Quantum mechanical calculations were performed using Guassian 03© software package Density Functional Theory (DFT) with B3YLP basis set was used to estimate the energy levels of Highest Occupied Molecular Orbital (HOMO) and Lowest Unoccupied Molecular Orbital (LUMO)

Why THz?

Unlike IR, Terahertz radiation is not absorbed by many materials including epoxy used in coating aluminum panels.

Materials that have unique spectral signature in Terahertz frequency include metals, water and other chemicals with strong intermolecular interactions.

How 8HQ (8-Hydroxyquinoline) will respond to THz?

The energy band gap between HOMO and LUMO is 4.8 eV

8HQ is an insulator and should be transparent to THz radiation.

How will the corrosion product be different from 8HQ?

The corrosion product aluminum hydroxide $Al(OH)_3$ is unstable and forms a bidendate complex in the presence of 8-Hydroxyquinoline ligands

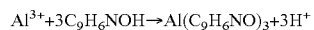

$$Al^{3+}+3C_9H_6NOH \rightarrow Al(C_9H_6NO)_3+3H^+$$

Energy band gap estimated using DFT calculation is 2.3 eV (<3.0 eV is a semiconductor)

Figure 2:
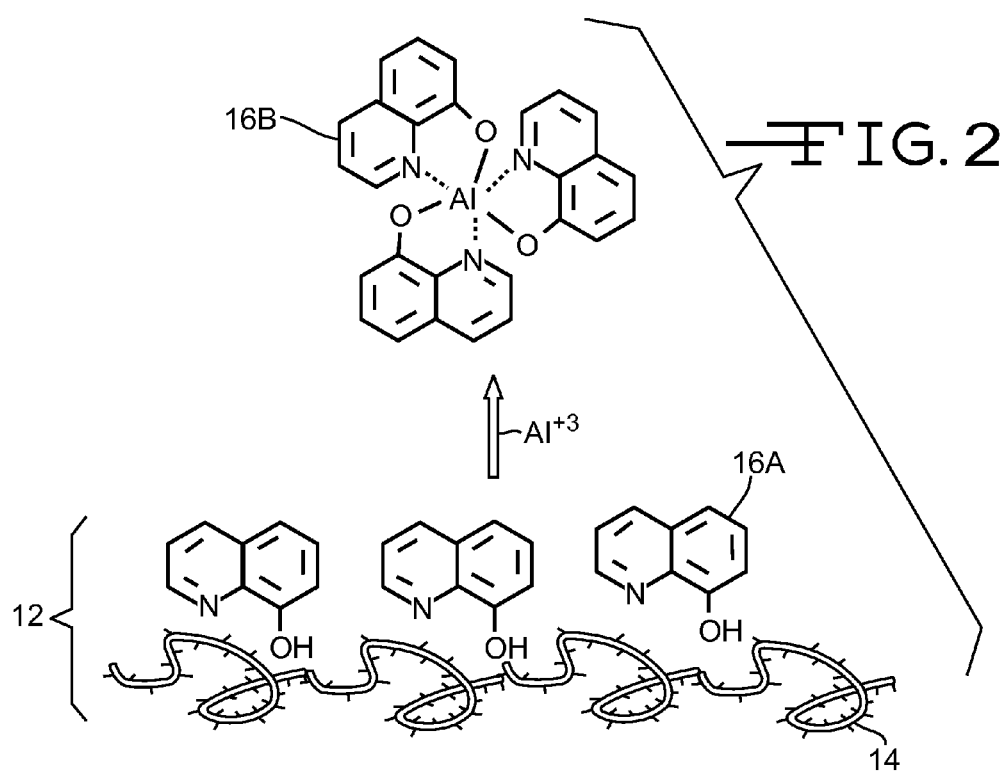

FIGS. 1 and 2 show an example of a corrosion detection product and method according to the invention. As shown in FIG. 1, an aluminum substrate 10 is coated with a corrosion detection coating 12. The substrate 10 gives off aluminum ions as it corrodes. The aluminum ions migrate into the coating 12. As shown in FIG. 2, the coating includes a film forming polymer 14 having molecules of a complexing agent 16A attached as side chains. The complexing agent 16A and the aluminum ions form a complex 16B when they come into contact with each other. The complex 16B fluoresces when it is exposed to ultraviolet or other radiation to enable the detection of corrosion.

The corrosion detection product and method are further illustrated by the following nonlimiting examples.

EXAMPLES

Example 1

A complexing agent, 8-hydroxyquinalone-5-sulfonic acid hydrate (HSAH), was added at 25% to water and dissolved by stirring with a magnetic stirrer (3.59 g HSAH to 24.0 g distilled water). This solution was added to 120.08 g of Flexbond 274 polyurethane emulsion. The materials were mixed thoroughly. It was found that the solution by itself did not fluoresce under UV light. An aluminum sulfate/water solution was made. A small amount of the two solutions were mixed and it was found that the mix showed a bright blue/green glow. The aluminum sulfate complexed the HSAH creating a clear material that fluoresced brightly when exposed to UV light.

The HSAH/Flexbond was applied as a coating, by HVLP sprayer, to an aluminum panel that had been primed with MIL-PRF-23377 primer. The coating (1 mil) was allowed to dry overnight and a topcoat of MIL-PRF-85285 epoxy top coat was applied. This panel was allowed to cure according to spec. Cross hatch adhesion testing was done and it was found the intermediate layer of HSAH/Flexbond solution caused some adhesion problems and topcoat removal was seen. This removal was rated 2B (15-25%) according to ASTM method D3359-02.

After cross hatch adhesion was complete, a few drops of the aluminum sulfate and water solution was dropped onto the cross hatch where the top coat was removed. This was to simulate the corrosion of the aluminum. When this area was exposed to the UV light, the exposed areas where the topcoat was removed fluoresced very well.

A second panel was prepped in the same manor with the HSAH sprayed between the primer and topcoat, except that the HSAH layer was applied at 2 mil thickness. This panel was scored with a blade and placed in a salt fog chamber with 5% salt fog and left for a period of 3 days. The panel was removed and exposed to UV light. The scored area showed a very slight fluoresce, an indication that corrosion had occurred and complexed the HSAH. The fluoresce was slight likely due to the low concentration levels of both the HSAH and the corrosion that was present.

Example 2

Corrosion Detection Coating Including
8-Hydroxyquinoline-5-Sulfonic Acid Complexing
Agent Dispersed in Water Based Polyurethane First disperse 3.59 g of 8-hydroxyquinoline-5-sulfonic acid hydrate (98%) into 24 g of distilled water, then combine with 120 g Flexbond 274 emulsion and magnetically mix thoroughly, to produce a corrosion detection coating according to the invention. On clean aluminum alloy panels spray a primer at 0.98 mils dry film thickness, then spray the corrosion detection coating at 0.98 mils dry film thickness, then allow the coating to dry before the final coating Defthane ELT. This coating system scored 15-35% removal with a cross hatch adhesion test according to ASTM D3359-02 Test method B.

Example 3

Corrosion Detection Coating Including
8-Hydroxyquinoline-5-Sulfonic Acid Complexing
Agent Dispersed in a Mixture of Water Based
Polyurethane and Carbodiimide Take 14.25 g of the corrosion detection coating described in Example 2 and add 0.75 g of Nisshinbo Carbodilite E-02 (~5% by weight) then thoroughly mix. On clean aluminum alloy panels spray a primer, then spray the corrosion detection coating with Carbodilite, then allow the coating to dry before the final coating of Defthane ELT. The Carbodilite enhanced coating has 0% coating removal with a crosshatch adhesion test and 0% cracking with a conical mandrel test.

Example 4

Corrosion Detection Coating Including
Immobilization of the Complexing Agent on Silica Step 1: In a 50 mL three neck round bottom flask fitted with a condenser, magnetic stir bar, and an adapter for thermocouple and inert gas inlet, was charged 2.5 gram of 2-amino-8-hydroxyquinoline and added 20 mL of dimethyl acetamide. The mixture was heated to 60° C. under argon and added 3.95 gram of 3-(triethoxysilyl)propyl isocyanate over a period of one hour. The reaction was continued for 12 hours and the product was stored. Infrared analysis of the product showed the absence of residual isocyanate group.

Step 2: In a glass vial containing 20 mL of distilled water, 0.12 gram of triethyl amine was added and mixed well. 5.0 gram of this solution was added slowly to another glass vial containing 1.0 gram of the product obtained from step 1. The reactants were mixed well on a stir plate for 12 hours. The product obtained was a colloidal dispersion of immobilized complexing agent on silica in water.

Coating formulation according to the invention: In a vial 20 grams of Flexbond and 1 gram of Carbodilite were charged and mixed well using a spatula. To this mixture, 4.6 gram of product obtained from step 2 was added with continuous mixing. This formulation was sprayed onto an aluminum panel and dried at room temperature for 24 hours. The coated panel was placed in 250 mL beaker containing 100 mL of water. After 24 hours, the panel was removed and kept aside. To the beaker containing 100 ml of water, was added 1 gram of aluminum sulfate and mixed well until it completely dissolved. This solution was exposed to UV lamp (365 nm) and there was no fluorescence. This test illustrates that the complexing agent was not leached out of the coating.

Control coating formulation: In a vial 20 grams of Flexbond and 1 gram of Carbodilite were charged and mixed well using a spatula. To this mixture, 0.6 gram of 8-hydroxyquinoline-5-sulfonic acid dissolved in 4 mL of water was added with continuous mixing. This formulation was sprayed onto an aluminum panel and dried at room temperature for 24 hours. The coated panel was placed in 250 mL beaker containing 100 mL of water. After 24 hours, the panel was removed and kept aside. To the beaker containing 100 ml of water, was added 1 gram of aluminum sulfate and mixed well till it completely dissolved. This solution was exposed to UV lamp (365 nm) and bluish green fluorescence was observed. This test illustrates that the complexing agent was leached out of the coating because it was not immobilized on a firm surface.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:
1. A corrosion detection method comprising:
providing a coating including a film forming material and a complexing agent, wherein the film forming material is a film forming polymer, the complexing agent being immobilized in the coating to reduce leaching;
applying the coating on a substrate that produces a corrosion byproduct which is a metal ion when it corrodes, the complexing agent and the corrosion byproduct forming a coordination complex when they come into contact with each other; and exposing the coating to radiation which causes the complex to be detectably different from the complexing agent in order to detect the corrosion, the radiation being terahertz rays.

2. The method of claim 1 wherein the complexing agent is immobilized by being part of the film forming polymer either in a main chain or a side chain.

3. The method of claim 2 wherein the film forming polymer includes molecules of the complexing agent attached as side chains to the main chain of the polymer.

4. The method of claim 1 wherein the coating further includes a water insoluble metal oxide, and wherein the complexing agent is immobilized by being tethered to the metal oxide.

5. The method of claim 4 wherein the water insoluble metal oxide is selected from the group consisting of titania, zirconia, silica, magnesia, alumina, and mixtures thereof.

* * * * *

UNITED STATES PATENT AND TRADEMARK OFFICE
CERTIFICATE OF CORRECTION

PATENT NO. : 8,623,653 B2  Page 1 of 1
APPLICATION NO. : 12/934369
DATED : January 7, 2014
INVENTOR(S) : Lalgudi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 223 days.

Signed and Sealed this
Twenty-second Day of September, 2015

Michelle K. Lee
*Director of the United States Patent and Trademark Office*